United States Patent
Aiken et al.

(10) Patent No.: US 8,436,184 B2
(45) Date of Patent: May 7, 2013

(54) 6-(BIPHENYL-ESTER)-3H-NAPHTHO[2,1-B]PYRANS AS PHOTOCHROMIC DICHROIC DYES AND OPTICAL ARTICLE CONTAINING THEM

(75) Inventors: Stuart Aiken, York (GB); Jean-Paul Cano, Charenton le Pont (FR); Christopher David Gabbutt, Preston (GB); Bernard Mark Heron, Brough (GB)

(73) Assignee: Essilor International (Compagnie Generale d'Optique, Charenton le Pont (FR)

( * ) Notice: Subject to any disclaimer, the term of this patent is extended or adjusted under 35 U.S.C. 154(b) by 266 days.

(21) Appl. No.: 12/439,324

(22) PCT Filed: Sep. 5, 2007

(86) PCT No.: PCT/EP2007/059298
§ 371 (c)(1),
(2), (4) Date: Oct. 9, 2009

(87) PCT Pub. No.: WO2008/028930
PCT Pub. Date: Mar. 13, 2008

(65) Prior Publication Data
US 2010/0039688 A1    Feb. 18, 2010

(30) Foreign Application Priority Data

Sep. 6, 2006  (WO) ................ PCT/IB2006/003684

(51) Int. Cl.
*C07D 401/00*    (2006.01)

(52) U.S. Cl.
USPC ..................................................... 546/196

(58) Field of Classification Search .................. None
See application file for complete search history.

(56) References Cited

U.S. PATENT DOCUMENTS

| | | | |
|---|---|---|---|
| 5,543,533 A | | 8/1996 | Allegrini et al. |
| 5,623,005 A | | 4/1997 | Rickwood et al. |
| 6,141,135 A | * | 10/2000 | Nagoh et al. ................ 359/241 |
| 6,630,597 B1 | | 10/2003 | Lin et al. |
| 2006/0006336 A1 | | 1/2006 | Cano et al. |
| 2010/0039688 A1 | | 2/2010 | Aiken et al. |
| 2010/0202033 A1 | | 8/2010 | Aiken et al. |

FOREIGN PATENT DOCUMENTS

| EP | 0 629 620 | 12/1994 |
|---|---|---|
| WO | 03/080595 | 10/2003 |

* cited by examiner

Primary Examiner — D M Seaman
Assistant Examiner — Heidi Reese
(74) Attorney, Agent, or Firm — Occhiuti Rohlicek & Tsao LLP

(57) ABSTRACT

A naphthopyran compound represented by the formula (I) wherein: $n_1$, $n_2$, p, m and q represent an integer; $R_1$, $R_2$ and $R_4$, represent a group selected from halogen, —$R_a$, —OH, —$OR_a$, —SH, —$SR_a$, —$NH_2$, —$NR_aR_{a1}$, —$NR_bR_c$, —CO—$R_a$, —$CO_2R_{a1}$, —OC(O)—$R_d$, —X—($R_e$)—Y, linear or branched ($C_1$-$C_{18}$) perfluoroalkyl group, wherein $R_a$, $R_{a1}$, $R_b$, $R_c$, X, Y, $R_e$, and $R_d$ are as defined in the description; Z represents a group selected from CO, CS, SO, $SO_2$, $CO_2$, C(O)S, $CS_2$, C(O)NH, C(O)$NR_a$, C(S)NH, C(S)$NR_a$ and C=$NR_a$; $R_3$ represents a group selected from halogen, —$R_a$, linear or branched ($C_{1-18}$) perfluoroalkyl group —OH, —$OR_a$, —SH, —$SR_a$, —$NH_2$, and —$NR_aR_{a1}$; $R_6$ represents a group selected from —$R_a$ which may be optionally substituted, linear or branched ($C_{1-18}$) perfluoroalkyl, cycloalkyl, heterocycloalkyl, aryl, and heteroaryl, which may be optionally substituted; $R_5$ represents a group selected from: halogen, —$R_a$, linear or branched ($C_{1-18}$) perfluoroalkyl group, —OH, —$OR_a$, —SH, —$SR_a$, —$NH_2$, —$NR_aR_{a1}$, —CO—$R_a$, —O—C(O)—$R_a$ and —$CO_2R_{a1}$; or when q is equal to 2, then two $R_5$ together represents further a group —O—($CH_2)_{q1}$—O— wherein q1 represents an integer comprised from 1 to 3 inclusive.

(I)

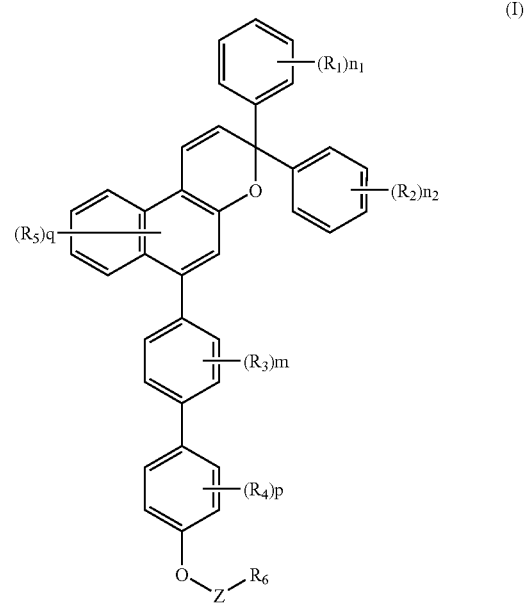

27 Claims, No Drawings

6-(BIPHENYL-ESTER)-3H-NAPHTHO[2,1-B]PYRANS AS PHOTOCHROMIC DICHROIC DYES AND OPTICAL ARTICLE CONTAINING THEM

CROSS-REFERENCE TO RELATED APPLICATIONS

This application is the National Stage of International Application No. PCT/EP2007/059298, filed Sep. 5, 2007, which claims priority to International Application No. PCT/IB2006/003684, filed Sep. 6, 2006. The contents of both applications are hereby incorporated by reference in their entirety.

The present invention relates to a group of novel dyes that are photochromic and to the use thereof in optical articles, especially in optical lenses such as ophthalmic lenses.

Photochromism is a well known physical phenomenon which is observed with certain classes of chemical compounds. A detailed discussion of this phenomenon can be found in "Photochromism: Molecules and Systems", Studies in Organic Chemistry 40, edited by H. Dürr and H. Bouas-Laurent, Elsevier, 1990.

A number of substituted 3H-naphtho[2,1-b]pyrans are known to be capable of exerting a reversible photochromic effect as described for example in WO 99/31082, U.S. Pat. No. 6,630,597, U.S. Pat. No. 5,552,090, U.S. Pat. No. 5,520,853, and U.S. Pat. No. 5,623,005. However, none of these 3H-naphtho[2,1-b]pyrans compounds are reported to have dichroic properties.

Passive photochromic devices, i.e. devices containing photochromic dyes whose absorbance depends only from the presence or absence of UV light, typically exhibit rather quick activation (coloration) but it generally takes several minutes or even tens of minutes to revert from the coloured to the bleached state. This slow fading is a severe drawback for the user of photochromic glasses who has to take them off to have clear vision when leaving the sunlight and entering dimmer light conditions.

The Applicants have undertaken extensive research aiming to provide new photochromic dyes exhibiting not only good photochromic properties, such as high absorption in the coloured state, fast colouring and fading rates, but which also may be capable of dichroism and linear light polarization when in a spatially ordered condition, for example when incorporated into liquid crystals or oriented polymer host materials.

The Applicants now have synthesized a group of new photochromic 3H-naphtho[2,1-b]pyrans having a mesogenic substituted biphenyl-ester group at C-6 of the naphthopyran nucleus. These new compounds have dichroic properties and some of them may be liquid at room temperature. These liquid photochromic dyes represent a specific embodiment of the present invention.

Incorporation of the biphenyl-ester moiety significantly improves the dichroic properties of the photochromic dyes in the activated state, and also influences the state of the dyes at room temperature. The new dyes when incorporated into anisotropic host materials such as liquid crystals or oriented polymers will strongly align with the host material molecules and exhibit strong dichroism, i.e. light polarizing, in the coloured state.

The Applicants further have observed that the new photochromic dyes of the present invention exhibit a fast fading rate, especially when dissolved in a fluid, mesomorphous or gel host medium, or even in the absence of a host medium at room temperature. They are able to revert from the coloured to the bleached state in a short time, typically in less than five minutes, which constitutes an important advantage over most of the prior art photochromic dyes.

Accordingly, the present invention provides a group of new naphthopyran compounds represented by the formula (I)

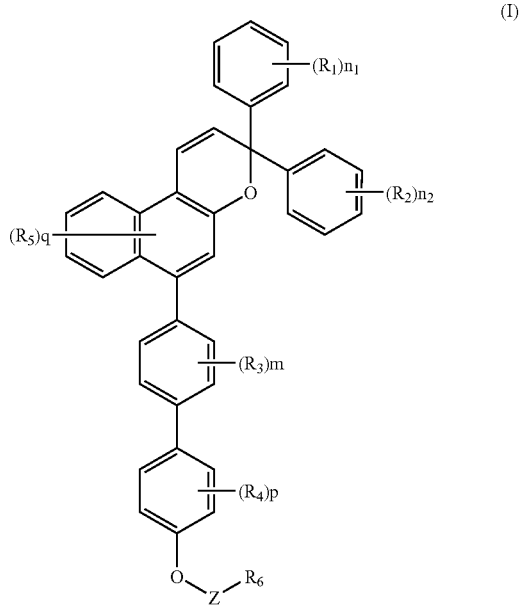

(I)

wherein:
$n_1$ is an integer comprised from 0 to 5 inclusive;
$n_2$ is an integer comprised from 0 to 5 inclusive;
p is an integer comprised from 0 to 4 inclusive;
m is an integer comprised from 0 to 4 inclusive;
q is an integer comprised from 0 to 5 inclusive;
$R_1$, $R_2$ and $R_4$, identical or different, independently from each other, represent a group selected from halogen, —$R_a$, —OH, —$OR_a$, —SH, —$SR_a$, —$NH_2$, —$NR_aR_{a1}$, —$NR_bR_c$, —CO—$R_a$, —$CO_2R_{a1}$, —OC(O)—$R_d$, —X—($R_e$)—Y, and linear or branched ($C_1$-$C_{18}$) perfluoroalkyl group, wherein:
$R_a$ represents a linear or branched ($C_{1-18}$) alkyl group;
$R_{a1}$ represents a group selected from hydrogen and linear or branched ($C_{1-18}$) alkyl group;
$R_b$ and $R_c$,
together and in combination with the nitrogen atom, represent a saturated 5 to 7 membered heterocyclic group which comprises optionally one additional heteroatom selected from O, N and S, and which may be optionally substituted by one or two group(s), identical or different, selected from halogen, —$R_a$, —OH, —$OR_a$, —$NH_2$, and —$NR_aR_{a1}$, wherein $R_a$ and $R_{a1}$ are as defined hereinbefore,
or together and in combination with the nitrogen atom and the adjacent phenyl group form a heterocyclic group of formula (A), (B), (C) or (D) wherein t is an integer comprised from 0 to 2 inclusive, and $R_a$ and $R_{a1}$ are as defined hereinbefore:

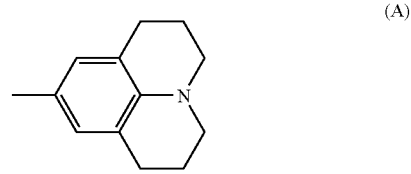

(A)

-continued

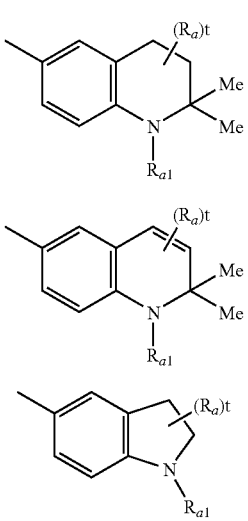

X represents a group selected from oxygen atom, —N($R_{a1}$)—, sulphur atom, —S(O)— and —S($O_2$)— wherein $R_{a1}$ is as defined hereinbefore;

Y represents a group selected from —$OR_{a1}$, —$NR_{a1}R_{a2}$, and —$SR_{a1}$ wherein $R_{a1}$ is as defined hereinbefore and $R_{a2}$ represent a group selected from hydrogen and linear or branched ($C_{1-18}$) alkyl group;

$R_e$ represents a linear or branched ($C_1$-$C_{18}$) alkylene group, which may be optionally substituted by a group selected from halogen, hydroxyl, linear or branched ($C_1$-$C_6$) alkoxy, and amino;

$R_d$ represents a group selected from linear or branched ($C_{1-18}$) alkyl group, —($R_e$)—Y, and aryl group which is optionally substituted by 1 to 4 groups selected from halogen, —$R_a$, —OH, —$OR_a$, —SH, —$SR_a$, —$NH_2$, —$NR_aR_{a1}$, —$NR_bR_c$, —CO—$R_a$, —$CO_2R_{a1}$ wherein $R_a$, $R_{a1}$, $R_b$, $R_c$, $R_d$, $R_e$ and Y are as defined hereinbefore;

$R_3$ represents a group selected from halogen, —$R_a$, linear or branched ($C_{1-18}$) perfluoroalkyl group —OH, —$OR_a$, —SH, —$SR_a$, —$NH_2$, and —$NR_aR_{a1}$, wherein $R_a$ and $R_{a1}$ are as defined hereinbefore;

$R_6$ represents a group selected from:
—$R_a$ which may be optionally substituted by a group selected from halogen, —OH, —$OR_a$, —SH, —$SR_a$, —$NH_2$, —$NR_aR_{a1}$, —CO—$R_a$, and —$CO_2R_{a1}$, wherein $R_a$ and $R_{a1}$ are as defined hereinbefore;
linear or branched ($C_{1-18}$) perfluoroalkyl group;
cycloalkyl, heterocycloalkyl, aryl, heteroaryl, which may be optionally substituted by 1 to 4 groups selected from halogen, —OH, —$OR_a$, —SH, —$SR_a$, —$NH_2$, —$NR_aR_{a1}$, —CO—$R_a$, —O—C(O)—$R_a$ and —$CO_2R_{a1}$, $R_5$ represents a group selected from:
halogen, —$R_a$, linear or branched ($C_{1-18}$) perfluoroalkyl group, —OH, —$OR_a$, —SH, —$SR_a$, —$NH_2$, —$NR_aR_{a1}$, —CO—$R_a$, —O—C(O)—$R_a$ and —$CO_2R_{a1}$ wherein $R_a$ and $R_{a1}$ are as defined hereinbefore,
or when q is equal to 2 and then two $R_5$ substituents are located onto two adjacent carbon atoms selected from C-7, C-8, C-9 and C-10 of the naphtho[2,1-b]pyran group, they may further represent together a group —O—($CH_2$)$_{q1}$—O— wherein q1 represents an integer comprised from 1 to 3 inclusive.

Z represents a group selected from CO, CS, SO, $SO_2$, $CO_2$, C(O)S, $CS_2$, C(O)NH, C(O)$NR_a$, C(S)NH, C(S)$NR_a$ and C=$NR_a$, wherein $R_a$ is as defined hereinbefore.

It is understood that in the present invention:
cycloalkyl means a 3 to 12 membered carbocycle, which may be monocyclic or bicyclic;
heterocycloalkyl means a cycloalkyl as defined hereinbefore comprising from 1 to 2 heteroatoms selected from oxygen, nitrogen and sulphur;
aryl means a phenyl group or a naphthyl group;
heteroaryl means a 3 to 10 membered monocycle or bicycle, which is comprised from 1 to 3 heteroatom(s) selected from oxygen, nitrogen and sulphur;
halogen means an atom selected from bromine, chloride, iodine, and fluorine.

Preferred naphthopyrans according to the present invention are compounds of formula (I), wherein:

$n_1$ is equal to 0 or 1, and $R_1$ represents a group selected from halogen, —OH and —$OR_a$ located at the para- or ortho-position of the phenyl group, wherein $R_a$ is as defined hereinbefore;

$n_2$ is equal to 1 and $R_2$ represents a group selected from halogen, —OH, —$OR_a$, and —$NR_bR_c$ located at the para-position of the phenyl group, wherein $R_a$, $R_b$ and $R_c$ are as defined hereinbefore;

m is equal to zero;

p is equal to zero;

q is an integer comprised from 0 to 2 inclusive, and $R_5$ represents a group selected from —OH and —$OR_a$ located on the C-8 and/or C-9 of the naphtho[2,1-b]-pyran group;

$R_6$ represents a group selected from —$R_a$, a linear or branched ($C_{1-18}$) perfluoroalkyl group, aryl, heteroaryl, which may be substituted by 1 to 4 groups selected from halogen and —$OR_a$ wherein $R_a$ is as defined hereinbefore; and Z represents a group selected from CO and $SO_2$.

Examples of most preferred compounds of formula (I) are the compounds represented by the following formulas (a) to (i):

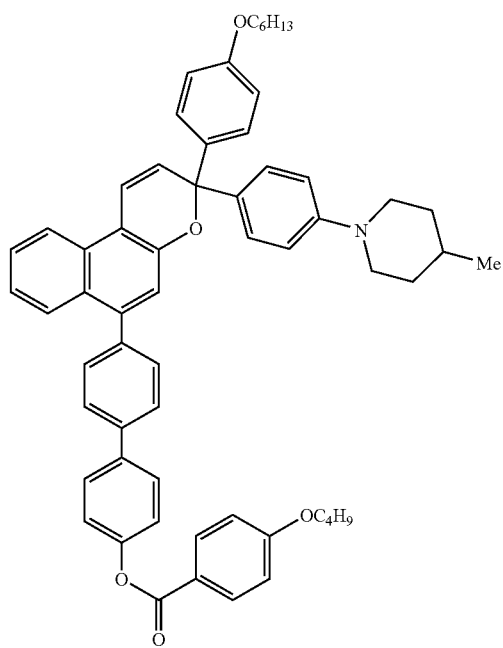

(a)

(b)
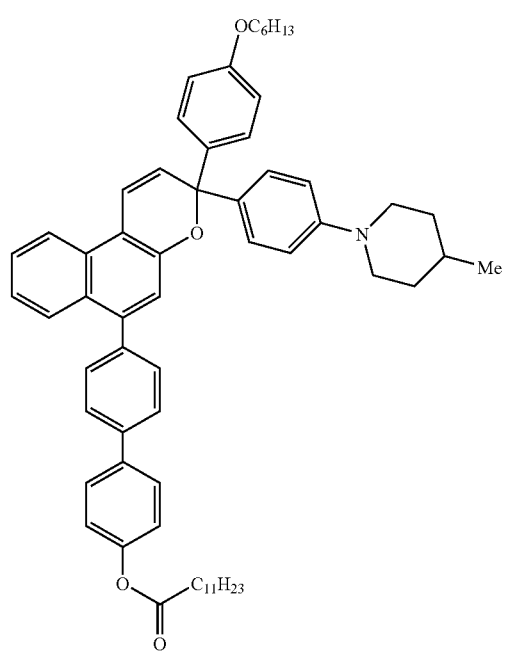
(c)
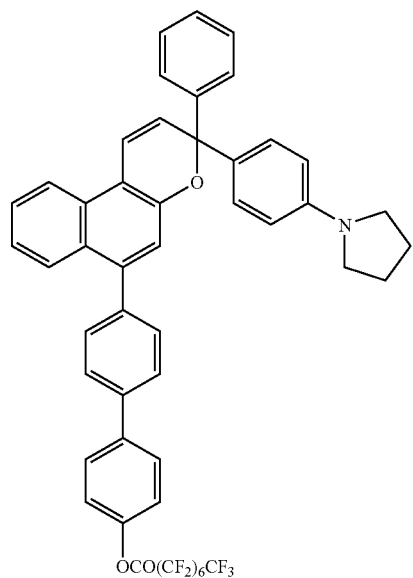
(d)
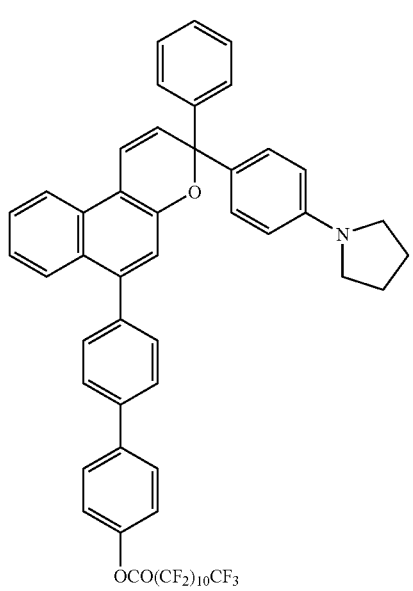
(e)
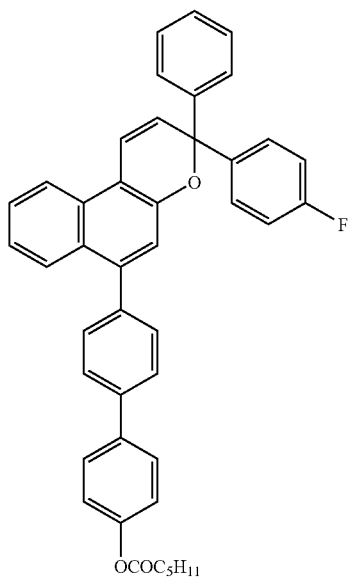

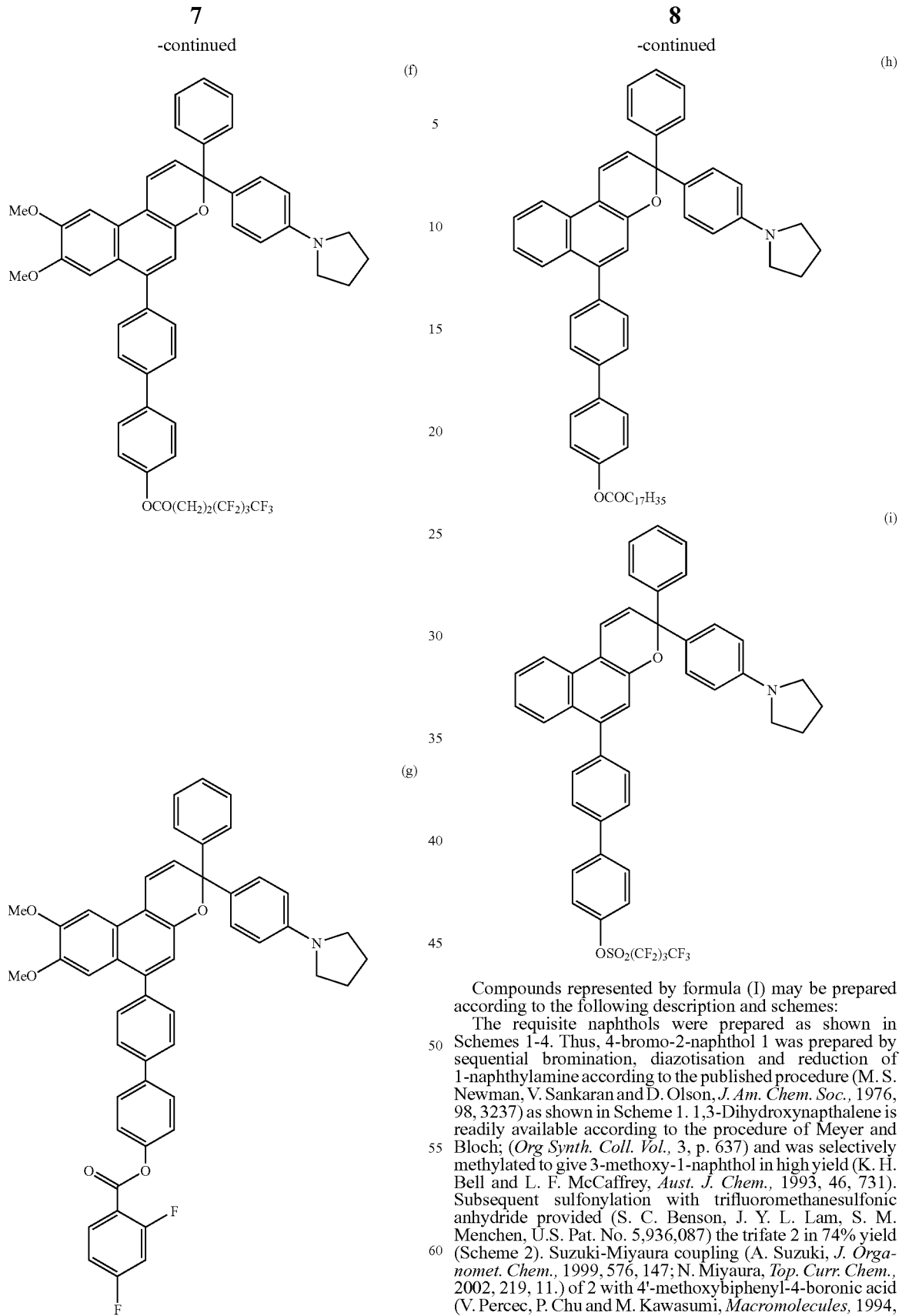

Compounds represented by formula (I) may be prepared according to the following description and schemes:

The requisite naphthols were prepared as shown in Schemes 1-4. Thus, 4-bromo-2-naphthol 1 was prepared by sequential bromination, diazotisation and reduction of 1-naphthylamine according to the published procedure (M. S. Newman, V. Sankaran and D. Olson, *J. Am. Chem. Soc.,* 1976, 98, 3237) as shown in Scheme 1. 1,3-Dihydroxynapthalene is readily available according to the procedure of Meyer and Bloch; (*Org Synth. Coll. Vol.,* 3, p. 637) and was selectively methylated to give 3-methoxy-1-naphthol in high yield (K. H. Bell and L. F. McCaffrey, *Aust. J. Chem.,* 1993, 46, 731). Subsequent sulfonylation with trifluoromethanesulfonic anhydride provided (S. C. Benson, J. Y. L. Lam, S. M. Menchen, U.S. Pat. No. 5,936,087) the trifate 2 in 74% yield (Scheme 2). Suzuki-Miyaura coupling (A. Suzuki, *J. Organomet. Chem.,* 1999, 576, 147; N. Miyaura, *Top. Curr. Chem.,* 2002, 219, 11.) of 2 with 4'-methoxybiphenyl-4-boronic acid (V. Percec, P. Chu and M. Kawasumi, *Macromolecules,* 1994, 27, 4441) gave 3 after treatment with excess boron tribromide (Scheme 3). The preparation of naphthol 4 involved an initial Claisen-type condensation of methyl (3,4-dimethoxyphenyl) acetate and 4'-bromoacetophenone mediated by sodium hydride (Scheme 4). Acylation reactions of this type of active CH compound have been reviewed (C. R. Hauser, F. W. Swamer and J. T. Adams, *Org. React.*, 1954, 8, 126; B. R. Davies and P. J. Garratt, *Comprehensive Organic Synthesis*, Pergamon, Oxford, 1991, vol. 2, p. 795). Cyclodehydration of the intermediate 1,3-diketone to 4 was accomplished under acidic conditions (A. V. Kel'in and Y. Yu. Kozyrkov *Synthesis*, 1998, 729, J. Lin and B. Van Gemert, PCT WO 99/31082). The preparation of 1,1-diarylprop-2-yn-1-ols 5 from lithium trimethylsilylacetylide and a benzophenone according to Scheme 5 has been documented (e.g. C. D. Gabbutt, J. D. Hepworth, B. M. Heron, S. M. Partington and D. A. Thomas, *Dyes Pigm.*, 2001, 49, 65). The preparation of the 6-substituted naphtho[2,1-b]pyrans is accomplished by the acid catalysed condensation of the appropriate 2-naphthol 1, 3 or 4 and alkynol derivatives 5 as shown in Scheme 6. This route to naphthopyrans has been reviewed (B. Van Gemert, *Organic Photochromic and Thermochromic Compounds Volume* 1: *Main Photochromic Families*, Ed. J. C. Crano and R. Gugglielmetti, Plenum Press, New York, 1998, p. 111; J. D. Hepworth and B. M. Heron, *Functional Dyes*, Ed. S.-H. Kim, Elsevier, Amsterdam, 2006, p. 85). The bromonaphthopyrans 6 and 8 are substrates for further modification by Suzuki-Miyaura coupling to the appropriate 4'-(trialkyl)silyloxy-4-biphenylboronic acid (see for example J-H. Ryu, J. Bae and M. Lee, *Macromolecules*, 2005, 38, 2050) and substituted 4-(trialkyl)silyloxyphenylboronic acid (see for examples D. J. Aitken, S. Faure and S. S. Roche, *Tetrahedron Lett.*, 2003, 44, 8827 and M. E. Hart et al. *J. Med. Chem.*, 2006, 49, 1101) to give, after removal of the silyl function, the 6-(4'-hydroxy-4-biphenyl)naphtho[2,1-b]pyrans which may be acylated with, for example, an acid halide in pyridine to afford the 6-(4'-acyloxy-4-biphenyl)naphtho[2,1-b]pyrans of general structure (I). Alternatively, the naphthopyran 7 can be similarly acylated as illustrated by examples (a) and (b). These three general sequences are shown in Scheme 7. More specifically, the Suzuki-Miyaura coupling of the 4-(triisopropylsilyloxy)phenylboronic acid to bromonaphthopyran derivative 8 with subsequent fluoride mediated removal of the triisopropylsilyl function is illustrated in Scheme 8.

Scheme 1

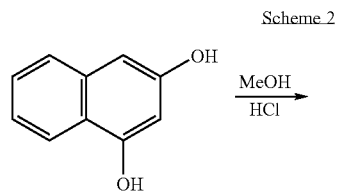

Scheme 2

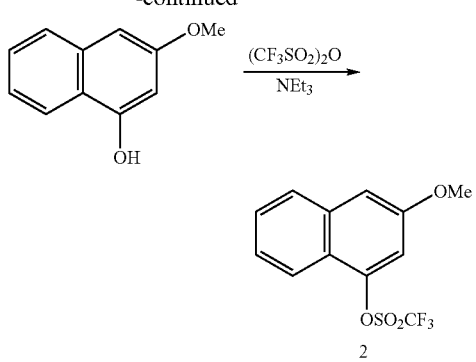

Scheme 3

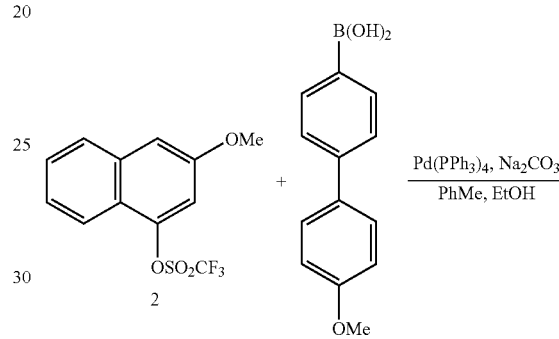

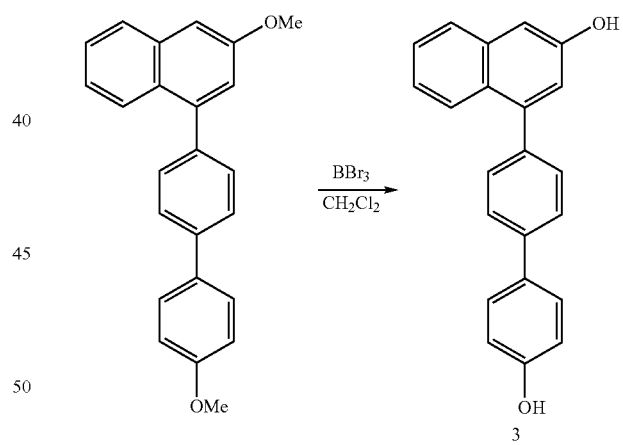

Scheme 4

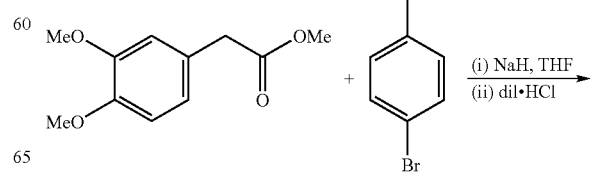

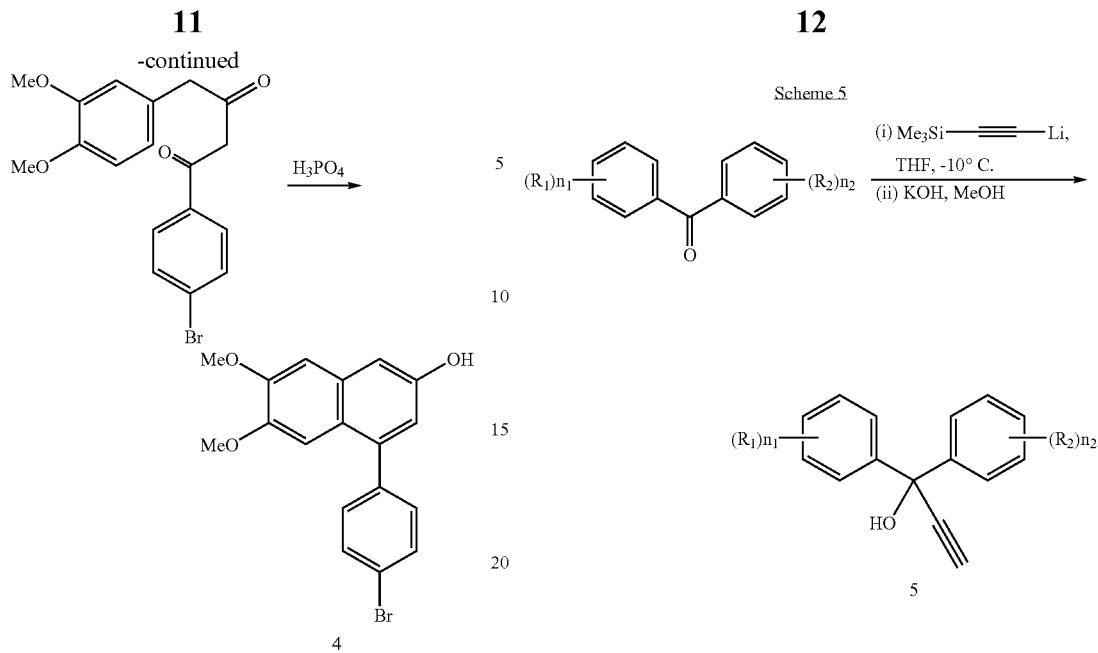
Scheme 5
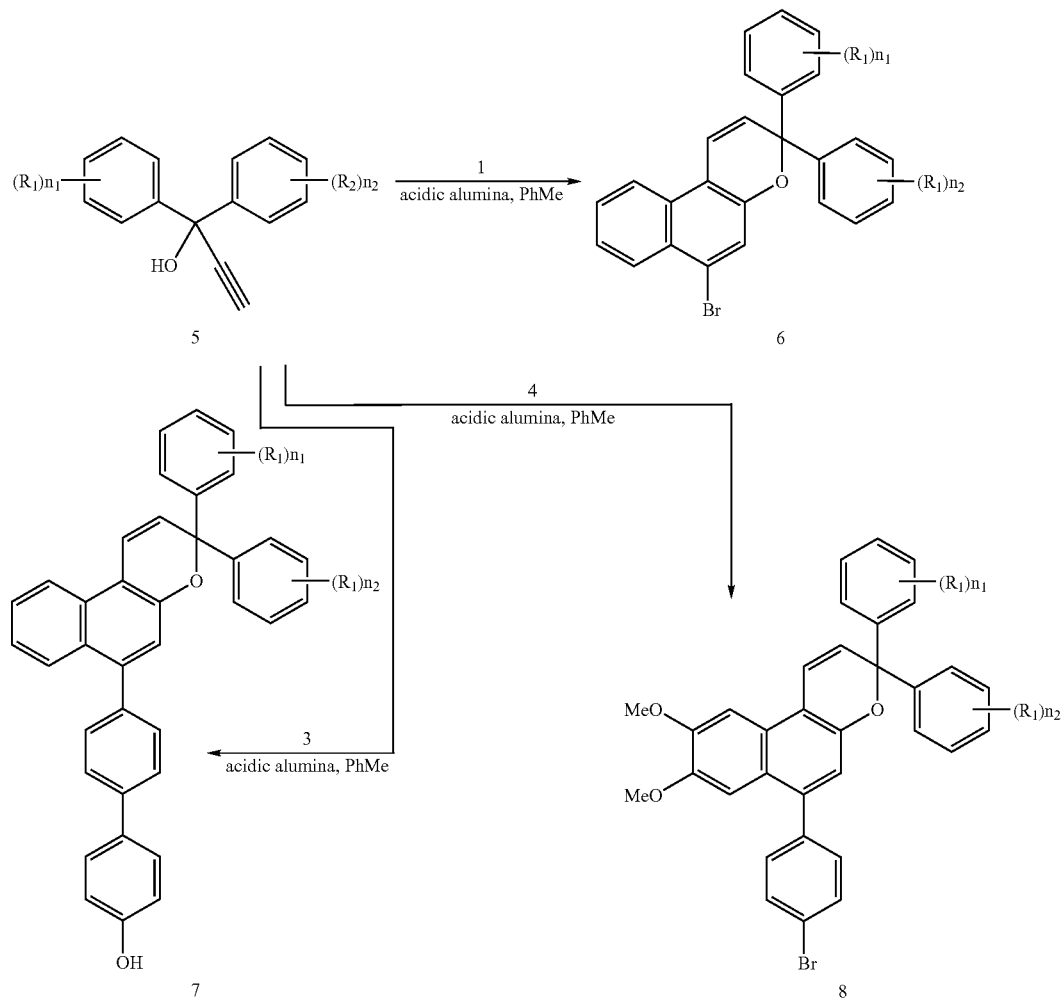
Scheme 6

Scheme 7
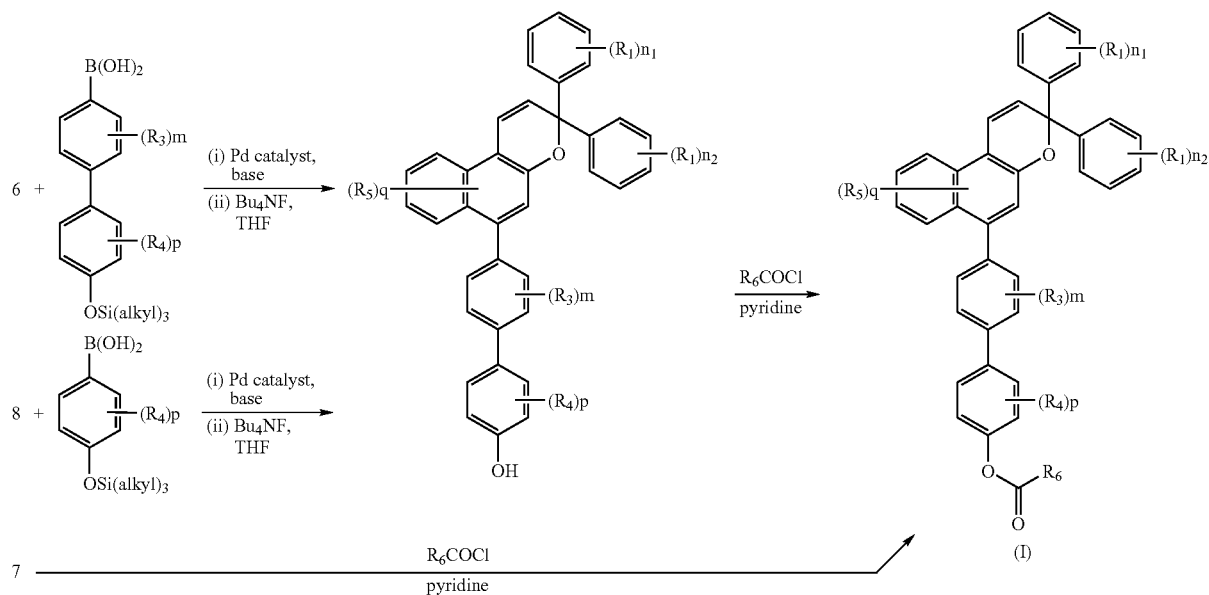
Scheme 8
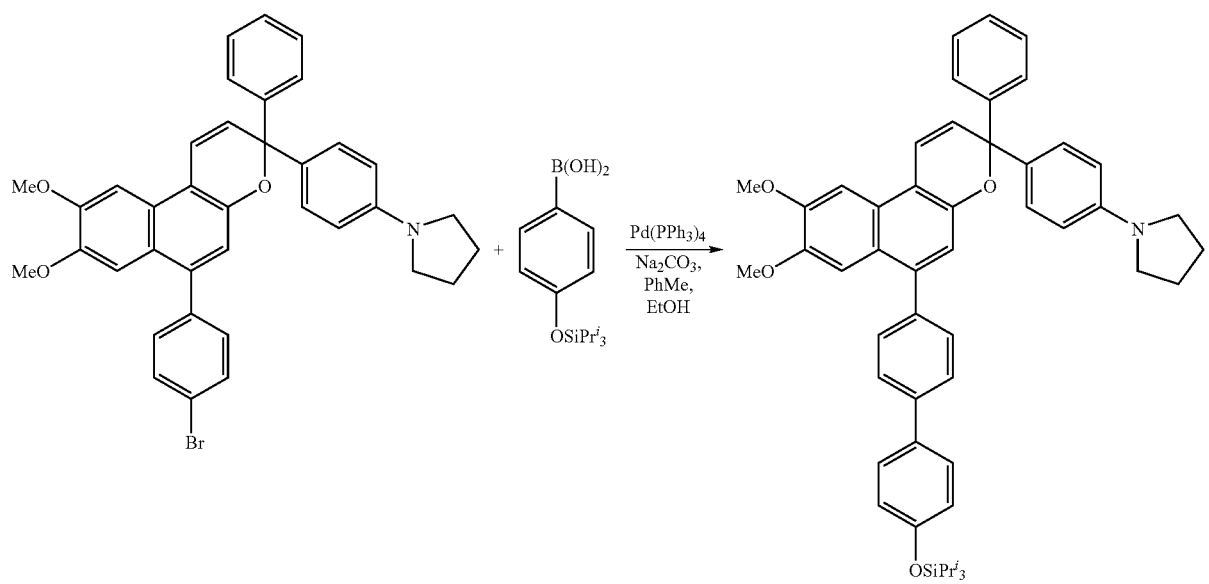

-continued

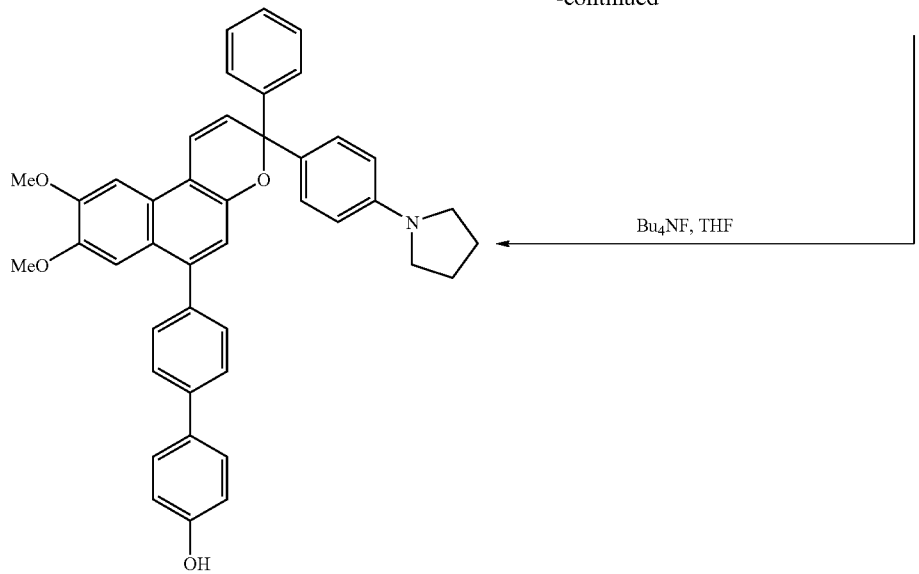

The photochromic compounds of the invention may be used alone, in combination with other biphenyl-ester naphthopyran of the invention, and/or in combination with one or more other appropriate complementary organic photochromic materials, i.e. an organic compound having at least one activated absorption maxima within the range of between about 400 to 700 nanometers. Compatible dyes or pigments may be also mixed with the photochromic dyes of the present invention, to achieve for example a more aesthetic result, a more neutral colour or absorb a particular wavelength of incident light, or to provide a desired hue.

The present invention also provides an optical article comprising one or more naphthopyran compounds (I) of the present invention. The naphthopyran compounds (I) of the present invention can be used in all kinds of optical devices and elements, such as ophthalmic elements and devices, display elements and devices, windows or mirrors. Non-limiting examples of ophthalmic elements include corrective and non-corrective lenses, including single vision or multi-vision lenses, which may be either segmented or non-segmented, as well as other elements used to correct, protect, or enhance vision, including without limitation contact lenses, intra-ocular lenses, magnifying lenses and protective lenses or visors. Non-limiting examples of display elements and devices include screens and monitors. Non-limiting examples of windows include automotive and aircraft transparencies, filters, shutters, and optical switches.

The optical article of the present invention is preferably a lens, and more preferably an ophthalmic lens.

When used in optical articles, the naphthopyran compounds can be incorporated, for example, in the bulk of a polymeric material of the optical article. Such a polymeric host material is generally a solid transparent or optically clear material. Preferred polymeric host materials are for example polymers of polyol(allyl carbonate) monomers, polyacrylates, poly(triethyleneglycol dimethacrylate), polyperfluoroacrylates, cellulose acetate, cellulose triacetate, cellulose acetate propionate, cellulose acetate butyrate, poly(vinyl acetate), poly(vinyl alcohol), polyurethanes, polycarbonates, poly(ethylene terephthalate), polystyrene, polyfluorostyrene, poly(diethylene glycol bis(alkyl carbonate)) and mixtures thereof.

The photochromic substances of the present invention may be incorporated into the polymeric host material by various methods described in the art. Such methods include dissolving or dispersing the photochromic substance within the host material by adding it to the monomeric host material prior to polymerization, or by imbibition of the photochromic substance into the host material by immersion of the host material in a hot solution of the photochromic substance.

In another preferred embodiment of the present invention the photochromic dyes are not incorporated into the bulk of an organic polymeric host material, but are incorporated into a surface coating or a film applied onto an optical substrate. The substrate is preferably a transparent or optically clear material, such as glass or organic polymers commonly used in optical applications.

The present invention of course also encompasses optical articles having at least one naphthopyran compound of formula (I) incorporated either in the bulk of the article, or in the coating of the article, or in the film applied onto the article.

In a still more preferred embodiment of the present invention, the coating or film incorporating the photochromic naphthopyran compounds of the present invention is an anisotropic film or coating, i.e. it comprises a layer or medium which is able to function as an alignment layer for the dye molecules. Such an alignment layer may be for example an organic polymer, such as polyvinyl alcohol (PVA). One common method of aligning the molecules of a dichroic dye involves heating a sheet or layer of PVA to soften the PVA and then stretching the sheet to orient the polymer chains. The dichroic dye is then impregnated into the stretched sheet and dye molecules take the orientation of the polymer chains. Alternatively, the dichroic dye can be first impregnated into the PVA sheet, and thereafter the sheet can be heated and stretched as described above to orient the PVA polymer chains and associated dyes. In this manner, the molecules of the dichroic dye can be suitably positioned or arranged within the oriented polymer chains of the PVA sheet and a net linear polarization can be achieved.

In an even more preferred embodiment of the present invention, the novel naphthopyran compounds are not incorporated into a solid, isotropic or anisotropic host material, but into a fluid, mesomorphous or gel host medium. Dissolving or dispersing the naphthopyran compounds of the present invention in such a fluid, mesomorphous or gel host medium increases the coloration rate and even more drastically the fading rate. The recovery time, i.e. the time it takes the material to revert from an absorptive condition to a clear condition, can thus be reduced to less than 5 minutes.

The fluid or mesomorphous host medium incorporating at least one naphthopyran compound is preferably selected from the group consisting of organic solvents, liquid crystals, and mixtures thereof.

The naphthopyran compounds of the present invention are preferably dissolved in the host medium.

The organic solvents may be selected for example from the group consisting of benzene, toluene, methyl ethyl ketone, acetone, ethanol, tetrahydrofurfuryl alcohol, N-methyl pyrrolidone, 2-methoxyethyl ether, xylene, cyclohexane, 3-methylcyclohexanone, ethyl acetate, ethyl phenylacetate, ethyl methoxyphenyl acetate, propylene carbonate, diphenylmethane, diphenylpropane, tetrahydrofuran, methanol, methyl propionate, ethylene glycol and mixtures thereof.

The liquid crystal medium that may be used in the present invention includes, without being limited to, such materials as nematic or chiral nematic media. Alternatively a polymeric liquid crystal medium can be used as the host material. These liquid crystal and polymeric liquid crystal media are generally used in combination with an organic solvent, for example one of the organic solvents mentioned above.

The mixture of a fluid, mesomorphous or gel host medium and at least one of the naphthopyran compounds of the present invention preferably is incorporated into a device containing a mechanism for holding the mixture in a mechanically stable environment.

A preferred device for holding the mixture in a mechanically stable environment is the one described in WO 2006/013250 and FR 2879757, which are hereby specifically incorporated by reference herein.

The preferred optical article of the present invention, disclosed in WO 2006/013250, comprises an optical component provided with at least one transparent cell arrangement juxtaposed in a parallel direction to the surface thereof, each cell being tightly closed and containing said fluid, mesomorphous or gel host medium and said at least one naphthopyran compound of the present invention. The transparent cell arrangement forms a layer whose height perpendicular to the component surface is less than 100 μm, preferably comprised between 1 μm and 50 μm.

The transparent cell arrangement may be formed either directly on a transparent rigid substrate of said optical component, or alternatively a transparent film incorporating the transparent cell arrangement may be applied on a transparent rigid substrate of the optical component.

The cell arrangement preferably occupies a large fraction of the total surface of the optical component. The ratio of the total surface occupied by the cells to the total surface of the optical component is preferably at least 90%, more preferable comprised between 90 and 99.5%, and most preferably between 96% and 98.5%.

The cell arrangement may be composed for example of hexagonal or rectangular cells, whose dimensions may be described by
 (a) their size parallel to the surface of the optical component, which is preferably of at least 1 μm, more preferably comprised between 5 μm and 100 μm;
 (b) the height of the cells perpendicular to the component surface, which is preferably less than 100 μm, and is more preferably comprised between 1 μm and 50 μm; and
 (c) the thickness of the partitions separating the tightly closed cells from each other, which is preferable comprised between 0.10 and 5.00 μm.

EXAMPLES

Synthesis of Intermediate Compounds used in the Synthesis of Example Compounds

3-Methoxynaphthalen-1-yl Trifluoromethanesulfonate

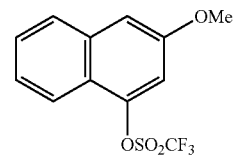

2

Trifluoromethanesulfonic anhydride (9.35 g, 32.8 mmol) was added dropwise to a solution of 3-methoxy-1-naphthol (5.77 g, 32.8 mmol) and $Et_3N$ (10 ml) in dichloromethane (100 ml) at 0° C. with stirring. After 1 h the resulting solution was washed with HCl (50 ml, 1 M) and saturated $Na_2CO_3$ (50 ml), dried ($MgSO_4$) and the solvent removed under reduced pressure. The residue was chromatographed on silica using EtOAc (7% in hexanes) to give the title compound (7.45 g, 74%) as a colourless oil.

3-Methoxy-1-(4'-methoxy-4-biphenyl)naphthalene

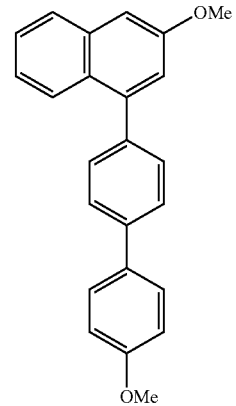 [SMILES: COc1ccc(-c2ccc(-c3cc(OC)cc4ccccc34)cc2)cc1]

A mixture of 3-methoxynaphthalen-1-yl trifluoromethanesulfonate (0.5 g, 1.7 mmol), (4'-methoxy-4-biphenyl)boronic acid (0.58 g, 2.5 mmol), $Na_2CO_3$ (0.27 g, 2.5 mmol) and $Pd(PPh_3)_4$ (40 mg, 2 mol %) in PhMe (20 ml) and EtOH (20 ml) under $N_2$ was heated at reflux. After 2 h the mixture was cooled, poured into water (100 ml), extracted with dichloromethane (3×50 ml), dried ($MgSO_4$) and the solvent removed under reduced pressure. The residue was dissolved in dichloromethane, filtered through a short plug of silica and the solvent removed under reduced pressure to give the title compound (0.44 g, 76%) as a colourless powder.

4-(4'-Hydroxy-4-biphenyl)-2-naphthol

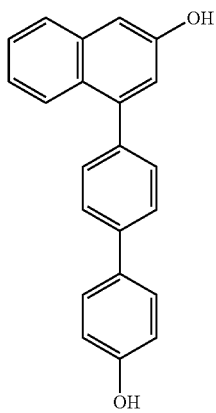

Boron tribromide (1.00 g, 3.9 mmol) was added dropwise to a solution of 3-methoxy-1-(4'-methoxy-4-biphenyl)naphthalene (0.44 g, 1.3 mmol) in dichloromethane (50 ml) at 0° C. under $N_2$. The solution was warmed to rt and stirring continued overnight, poured into water (200 ml), extracted with $Et_2O$ (3×50 ml), dried ($MgSO_4$) and the solvent removed under reduced pressure to give the title compound (0.40 g, 100%) as a brown powder.

1-(4-Bromophenyl)-4-(3,4-dimethoxyphenyl)butane-1,3-dione

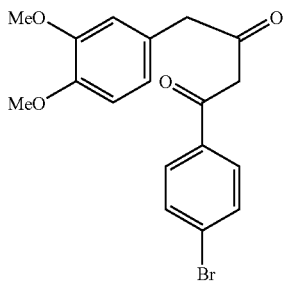

Sodium hydride (60% dispersion, 3.80 g, 95.1 mmol) was added portionwise to methyl 2-(3,4-dimethoxyphenyl)acetate (10 g, 47.6 mmol) in $Et_2O$ (100 ml) at 0° C. A solution of 4'-bromoacetophenone (9.48 g, 47.6 mmol) in $Et_2O$ (50 ml) was added dropwise over 1 h. The mixture was heated at reflux for 16 h, cooled, poured into ice/HCl (2 M), extracted with $Et_2O$ (3×100 ml), dried ($MgSO_4$) and the solvent removed under reduced pressure. The residue was crystallized from MeOH to give the title compound (9 g, 50%) as a tan powder.

4-(4-Bromophenyl)-6,7-dimethoxy-2-naphthol

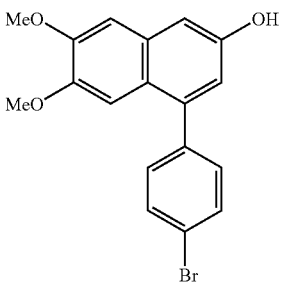

1-(4-Bromophenyl)-4-(3,4-dimethoxyphenyl)butane-1,3-dione (3 g, 8 mmol) in 85% phosphoric acid was heated at 70° C. for 20 h. The resulting solution was cooled, poured into water (150 ml) and filtered. The residue was dissolved in dichloromethane (50 ml), washed with water (50 ml), dried ($MgSO_4$) and the solvent was removed under reduced pressure to give the title compound (2.56 g, 90%) as a brown powder.

General Procedure for the Synthesis of 6-bromophenyl-8,9-dimethoxynaphtho[2,1-b]pyrans A mixture of 4-(4-bromophenyl)-6,7-dimethoxy-2-naphthol (9.7 mmol), 1,1-diarylprop-2-yn-1-ol (9.7 mmol) and acidic alumina (3 g) in toluene (100 ml) was heated at reflux. After 2 h the solution was filtered hot and the residue was washed with PhMe (50 ml). The solvent was removed under reduced pressure and the residue chromatographed on silica. The solvent was removed under reduced pressure and the residue was washed with MeOH to give the title compound which was purified by flash chromatography from silica gel. The following compounds were prepared in this way:

6-(4-Bromophenyl)-8,9-dimethoxy-3-phenyl-3-(4-pyrrolidinophenyl)-3H-naphtho[2,1-b]pyran dichloromethane as eluent, 64% as a violet powder

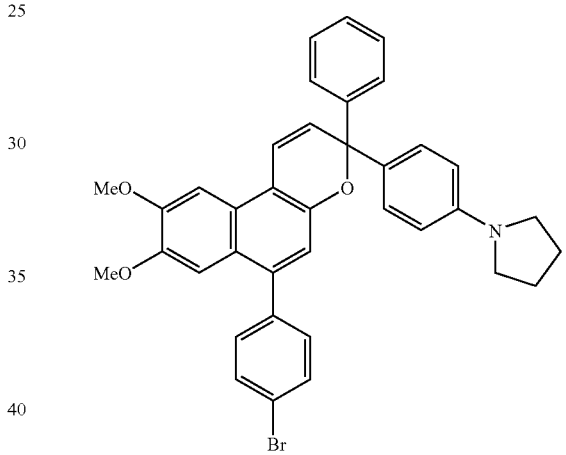

6-(4-Bromophenyl)-8,9-dimethoxy-3-(4-butoxyphenyl)-3-(9-julolidinyl)-3H-naphthol[2,1-b]pyran dichloromethane as eluent, 51% as a green powder

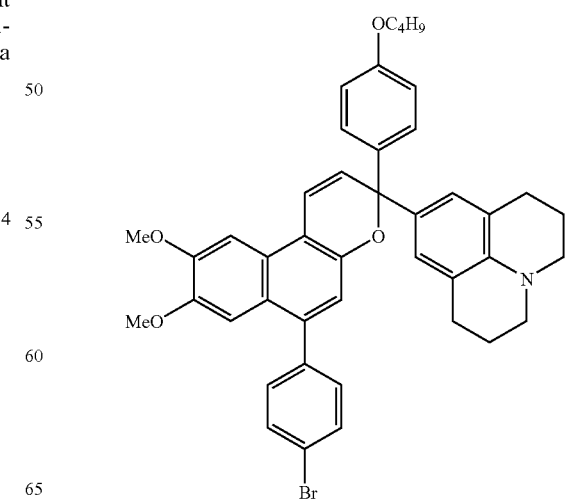

8,9-Dimethoxy-3-phenyl-3-(4-pyrrolidinophenyl)-6-[(4'-(triisopropylsilyloxy)-4-biphenyl)]-3H-naphtho[2,1-b]pyran

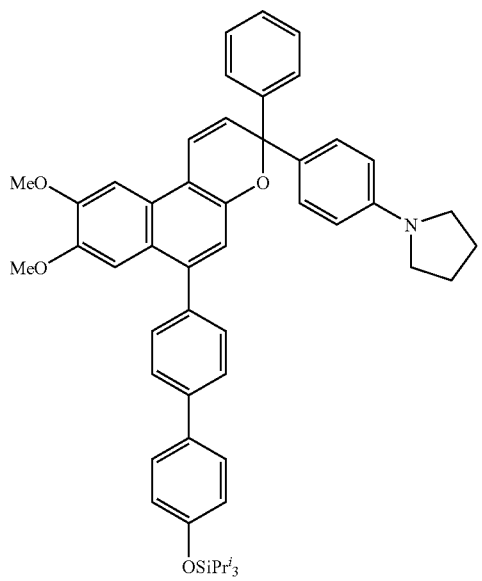

A mixture of 6-(4-bromophenyl)-8,9-dimethoxy-3-phenyl-3-(4-pyrrolidinophenyl)-3H-naphtho[2,1-b]pyran (2.4 mmol), and a 4-(triisopropylsilyloxy)phenylboronic acid (3.6 mmol) in 1,2-dimethoxyethane (50 ml) was degassed by purging with $N_2$. Tetrakis(triphenylphosphine)palladium(0) (5 mol %) was added followed by $Na_2CO_3$ (7.2 mmol) in degassed water (50 ml). The mixture was heated at 100° C. for 16 h, cooled, poured into water, extracted with dichloromethane (5×50 ml), dried ($MgSO_4$) and the solvent removed under reduced pressure. The residue was chromatographed on silica using dichloromethane as eluent. The solvent was removed under reduced pressure and the residue crystallised from acetone-methanol by slow evaporation to give the title compound 70% as a colourless powder.

8,9-Dimethoxy-6-[(4'-(hydroxy)-4-biphenyl)]-3-phenyl-3-(4-pyrrolidinophenyl)-3H-naphtho[2,1-b]pyran

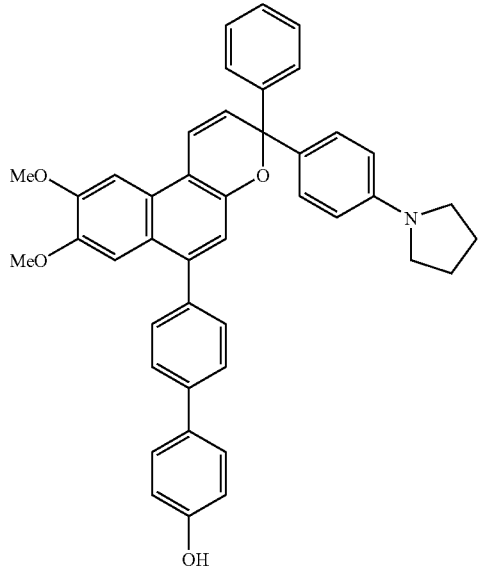 [SMILES: COc1cc2c(-c3ccc(-c4ccc(O)cc4)cc3)cc3c(c2cc1OC)C=CC(c1ccccc1)(c1ccc(N2CCCC2)cc1)O3]

A solution of tetrabutylammonium fluoride (1M in THF) (1.26 mmol) was added to a solution of 8,9-dimethoxy-3-phenyl-3-(4-pyrrolidinophenyl)-6-[(4'-(triisopropylsilyloxy)-4-biphenyl)]-3H-naphtho[2,1-b]pyran (1.26 mmol) in THF (30 ml) with stirring. After 5 min HCl (3 ml, 1 M) was added and the solvent removed under reduced pressure. The residue was chromatographed on silica using dichloromethane (70% in hexanes) as eluent The solvent was removed under reduced pressure and the residue crystallised from acetone/MeOH to give the title compound (57%) as a cream powder, mp 154-155° C.

3-[4-(Hexyloxy)phenyl]-3-[(4-methylpiperidino)phenyl]-6-(4'-hydroxy-4-biphenyl)-3H-naphtho[2,1-b]pyran

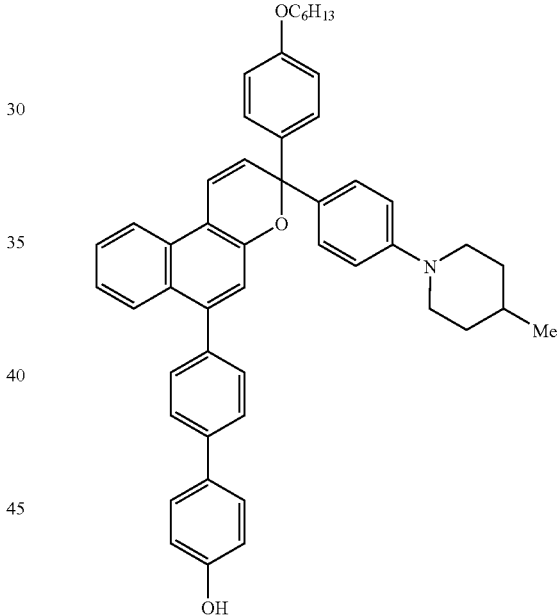

A mixture of 4-(4'-hydroxy-4-biphenyl)-2-naphthol (1.60 g, 5.1 mmol), 1-[4-(hexyloxy)phenyl]-1-[4-(4-methylpiperidin-1-yl)phenyl]prop-2-yn-1-ol (2.08 g, 5.1 mmol) and alumina (3 g) in toluene (250 ml) was heated at reflux. After 2 h the solution was filtered hot, the solvent was removed under reduced pressure and the residue was chromatographed on silica using EtOAc (10-20% in hexanes) as eluent. The solvent was removed under reduced pressure and the residue crystallized from AcMe/MeOH to give the title compound (1.94 g, 54%) as a blue powder.

3-(4-fluorophenyl)-6-(4'-hydroxybiphen-4-yl)-3-phenyl-3H-naphtho[2,1-b]pyran

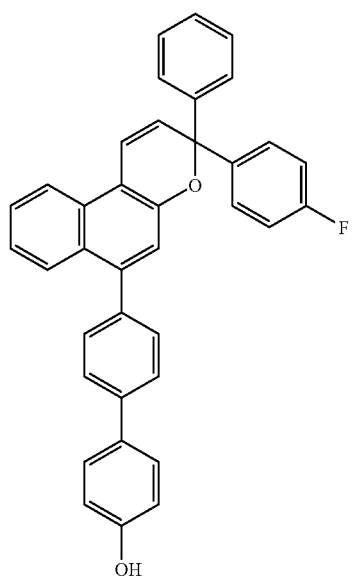 [SMILES: Oc1ccc(-c2ccc(-c3cc4c(c5ccccc35)C=CC(c3ccccc3)(c3ccc(F)cc3)O4)cc2)cc1]

A solution of 4-(4'-hydroxy-4-biphenyl)-2-naphthol (16.14 g, 52 mmol), 1-(4-fluorophenyl)-1-phenylprop-2-yn-1-ol (11.7 g, 52 mmol) and toluene-4-sulphonic acid (0.05 g) in toluene (200 mL) was heated at reflux. After 2 h the mixture was poured into saturated sodium bicarbonate solution (400 mL), extracted with dichloromethane (DCM) (4×100 mL), dried (MgSO$_4$) and the solvent removed under reduced pressure. The residue was chromatographed on silica using EtOAc (10-30% in hexanes) to afford 3-(4-fluorophenyl)-6-(4'-hydroxybiphen-4-yl)-3-phenyl-3H-naphtho[2,1-b]pyran which was collected, the solvent removed under reduced pressure, the residue was filtered through a short plug of silica using DCM as eluent and the solvent removed under reduced pressure to give the title compound (19.37 g, 72%) as an orange solid which was used without further purification.

6'[4'-(hydroxy)biphenyl-4-yl]-3-phenyl-3-(4-pyrrolidinophenyl)-3H-naphto[2,1-b]pyran This compound is obtained from 4-(4'-hydroxy-4-biphenyl)-2-naphthol and 1-(4-pyrrolidinophenyl)-1-phenyl-prop-2-yn-1-ol according to procedure for the synthesis of 3-(4-fluorophenyl)-6-(4'-hydroxybiphen-4-yl)-3-phenyl-3H-naphtho[2,1-b]pyran.

Example (a)

6-[4'-(4-Butoxybenzoyloxy)-4-biphenyl]-3-[4-(hexyloxy)phenyl]-3-[4-(4-methylpiperidino)phenyl]-3H-naphtho[2,1-b]pyran

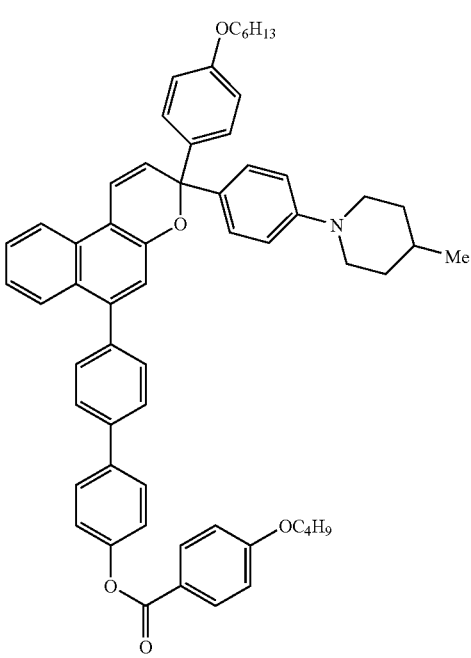

(a)

4-Butoxybenzoyl chloride (0.18 g, 0.06 mmol) was added dropwise to a solution of 3-[4-(hexyloxy)phenyl]-3-[4-(4-methylpiperidino)phenyl]-6-(4'-hydroxy-4-biphenyl)-3H-naphtho[2,1-b]pyran (0.6 g, 0.86 mmol) in dichloromethane (50 ml) containing pyridine (0.2 ml) at rt. After stirring for 2 h the solution was poured into HCl (2 M, 40 ml), extracted with dichloromethane (3×30 ml), dried (MgSO$_4$), the solvent removed under reduced pressure and the residue chromatographed on silica using EtOAc (20% in hexanes) as eluent. The solvent was removed under reduced pressure and the residue crystallized from AcMe/EtOH to give the title compound (0.10 g, 13%) as colourless plates, mp 92-94° C.

Example (b)

6-[4'-(4-Dodecanoyloxy)-4-biphenyl]-3-[4-(hexyloxy)phenyl]-3-[4-(4-methylpiperidino)phenyl]-3H-naphtho[2,1-b]pyran

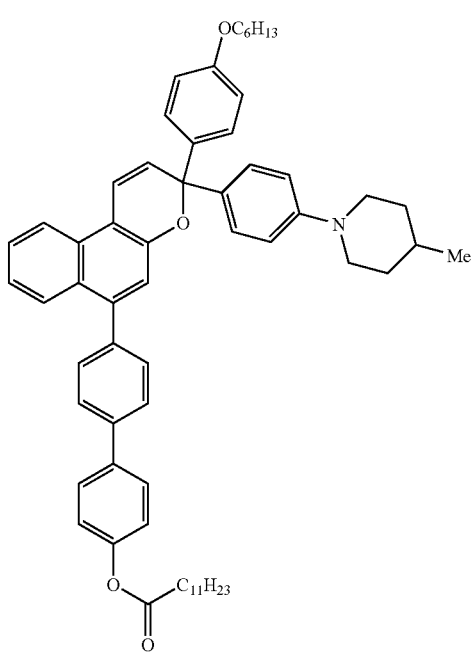

(b)

Dodecanoyl chloride was added dropwise to a solution of 3-[4-(hexyloxy)phenyl]-3-[4-(4-methylpiperidino)phenyl]-6-(4'-hydroxy-4-biphenyl)-3H-naphtho[2,1-b]pyran (0.5 g, 0.7 mmol) in DCM (30 ml) and pyridine (1 ml) at rt. The resulting solution was stirred for 1 h, poured into HCl (2 M, 100 ml), extracted with dichloromethane (3×30 ml), washed with NaOH (2 M, 100 ml), dried (MgSO$_4$) and the solvent removed under reduced pressure. The residue was chromatographed on silica using EtOAc (20-100% gradient in hexanes) and the solvent removed under reduced pressure to give the title compound (0.30 g, 48%) as a viscous oil.

Example (c)

6-[4'-(perfluorooctanoyloxy)biphen-4-yl]-3-phenyl-3-(4-pyrrolidino-phenyl)-3H-naphtho[2,1-b]pyran

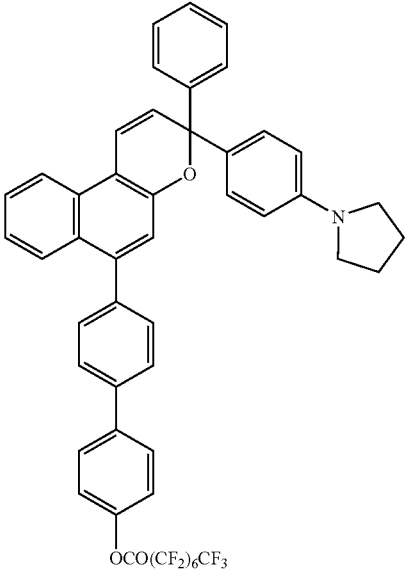

(c)

2,2,3,3,4,4,5,5,6,6,7,7,8,8,8-Pentadecafluoro-octanoyl chloride (0.30 g, 0.7 mmol) was added to a solution of 6-[4'-(hydroxy)biphen-4-yl]-3-phenyl-3-(4-pyrrolidinophenyl)-3H-naphtho[2,1-b]pyran (0.40 g, 0.7 mmol) in DCM (30 mL) containing pyridine (2 mL) under N$_2$ at 0° C. with stirring. The mixture was stirred at room temperature for 1 h, poured into HCl (2 M, 100 mL), extracted with DCM (3×50 mL), washed with water (100 mL), dried (MgSO$_4$) and the solvent removed under reduced pressure. The residue was filtered through a short plug of silica using DCM (60% in hexanes) as eluent and the solvent removed under reduced pressure. The residue was dissolved in Et$_2$O, hexane was added and the solvent reduced. The resulting precipitate was filtered to give the title compound (0.17 g, 25%) as a colourless powder, mp 144-145° C.

Example (d)

6-[4'-(perfluorododecanoyloxy)biphen-4-yl]-3-phenyl-3-(4-pyrrolidino-phenyl)-3H-naphtho[2,1-b]pyran

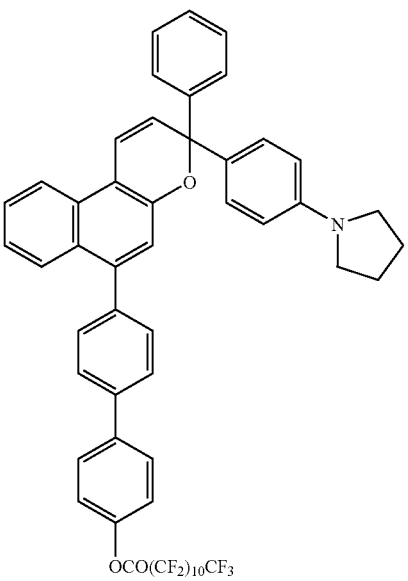

(d)

Solid 2,2,3,3,4,4,5,5,6,6,7,7,8,8,9,9,10,10,11,11,12,12,12-tricosafluorododecanoyl chloride (0.37 g, 0.58 mmol) was added to a solution of 6-[4'-(hydroxy)biphen-4-yl]-3-phenyl-3-(4-pyrrolidinophenyl)-3H-naphtho[2,1-b]pyran (0.33 g, 0.58 mmol) in DCM (100 mL) containing 4-dimethylaminopyridine (0.05 g) and pyridine (2 mL) under $N_2$ with stirring. The mixture was stirred at room temperature for 3 h, poured into HCl (2 M, 100 mL), extracted with EtOAc (3×30 mL), washed with water (100 mL), dried (MgSO$_4$) and the solvent removed under reduced pressure. The residue was filtered through a short plug of silica using DCM (60% in hexanes as eluent), the solvent removed under reduced pressure. Hexane was added and the resulting solid filtered to give the title compound (0.31 g, 46%) as a colourless powder, mp 129-130° C.

Example (e)

3-(4-fluorophenyl)-6-(4'-(hexanoyloxy)biphen-4-yl)-3-phenyl-3H-naphtho[2,1-b]pyran

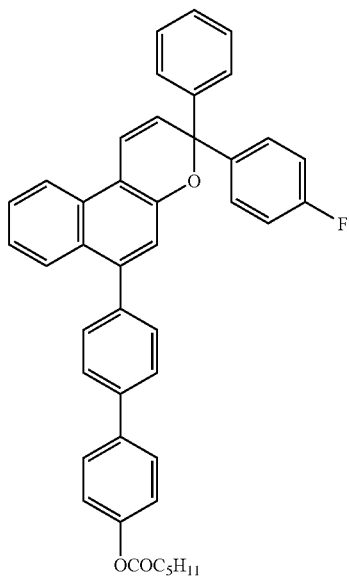

(e)

Hexanoyl chloride (5.01 g, 37 mmol) was added dropwise to a solution of 3-(4-fluorophenyl)-6-(4'-hydroxybiphen-4-yl)-3-phenyl-3H-naphtho[2,1-b]pyran (19.37 g, 37 mmol) in DCM (100 mL) containing pyridine (20 mL) at 0° C. After ½ h additional hexanoyl chloride (5.01 g, 37 mmol) was added. Stirring was continued for a further ½ h more, the solution was poured into HCl (2 M, 400 mL), separated and extracted with DCM (2×100 mL), the combined organic phases were washed with water saturated sodium bicarbonate (200 mL), dried (MgSO$_4$) and the solvent removed under reduced pressure. The residue was filtered through a short plug of silica using DCM (50% in hexanes) as eluent. The solvent was removed under reduced and the residue triturated alternately with hexanes and methanol twice. The residue was dried under vacuum to give the title compound (16.51 g, 72%) as a yellow foam, mp 64-65° C.

Example (f)

8,9-dimethoxy-6-[4'-(4,4,5,5,6,6,7,7,7-nonafluoro-heptanoyloxy)biphen-4-yl]-3-phenyl-3-(4-pyrrolidinophenyl)-3H-naphtho[1,2-b]pyran

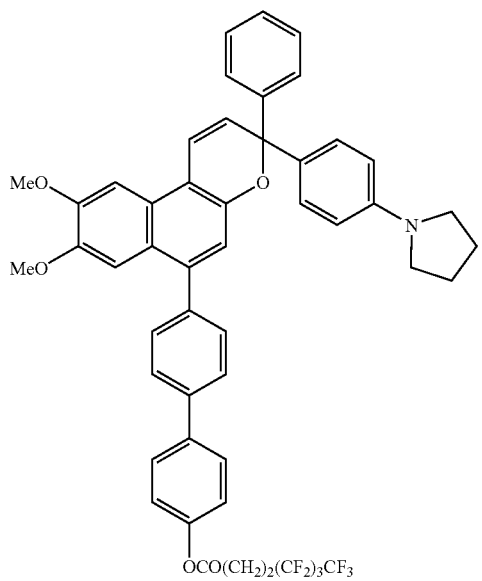

(f)

A solution of 8,9-dimethoxy-6-[4'-hydroxyoxybiphen-4-yl]-3-phenyl-3-(4-pyrrolidinophenyl)-3H-naphtho[1,2-b]pyran (0.95 g, 1.5 mmol) and 4,4,5,5,6,6,7,7,7-nonafluoro-heptanoic acid (0.53 g, 1.8 mmol) in DCM (20 mL) containing 4-dimethylaminopyridine (0.02 g) and N,N'-dicyclohexylcarbodiimide (0.33 g, 1.6 mmol) under $N_2$ was stirred at room temperature for 1 h. The resulting mixture was filtered through a short plug of silica using EtOAc (5% in DCM) as eluent. The solvent was removed under reduced pressure and the residue chromatographed on silica using EtOAc (0-25% gradient in toluene) as eluent. The solvent was removed under reduced pressure and the residue washed with toluene/hexanes to give the title compound (0.69 g, 51%) as a pale violet powder, mp 218-219° C. The liquors provided a further 0.16 g (12%) after evaporation and washing with acetone.

Example (g)

8,9-dimethoxy-6-[4'-(2,4-difluorobenzoyloxy)biphen-4-yl]-3-phenyl-3-(4-pyrrolidinophenyl)-3H-naphtho[1,2-b]pyran

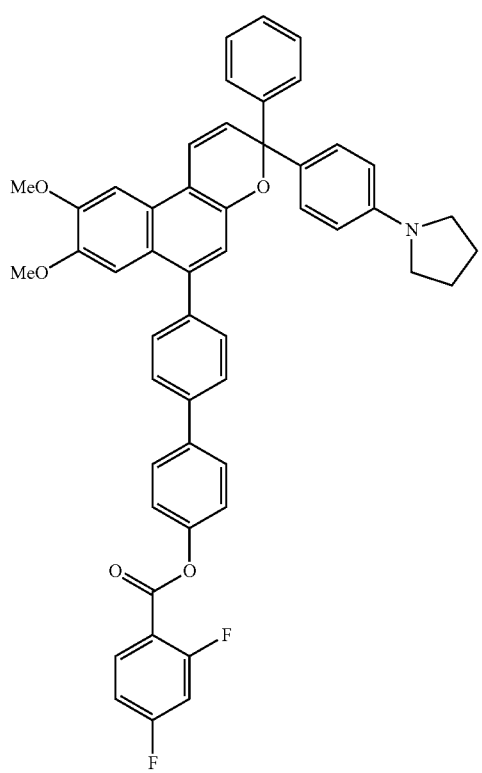

(g)

A solution of 8,9-dimethoxy-6-[4'-hydroxybiphen-4-yl]-3-phenyl-3-(4-pyrrolidinophenyl)-3H-naphtho[1,2-b]pyran (0.95 g, 0.5 mmol) and 2,4-difluorobenzoic acid (0.09 g, 0.5 mmol) in DCM (40 mL) containing 4-dimethylaminopyridine (0.01 g) and N,N'-dicyclohexylcarbodiimide (0.11 g, 1.6 mmol) under $N_2$ was stirred at room temperature for 2 h. The resulting mixture was filtered through a short plug of silica using DCM as eluent. The solvent was removed under reduced pressure and the residue chromatographed on silica using EtOAc (0-20% gradient in toluene) as eluent. The solvent was removed under reduced pressure and the residue washed with acetone to give the title compound (0.29 g, 70%) as a pale violet powder, mp 249-250° C.

Example (h)

6-[4'-(stearoyloxy)biphen-4-yl]-3-phenyl-3-(4-pyrrolidinophenyl)-3H-naphtho[2,1-b]pyran

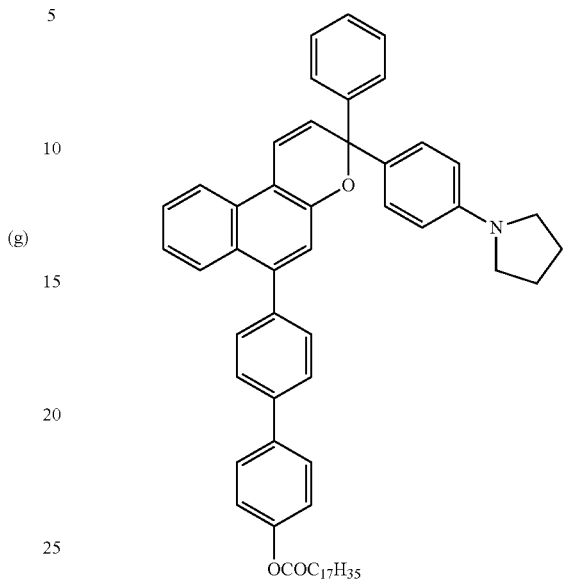

Stearoyl chloride (0.31 g, 1 mmol) was added to a solution of 6-(4-hydroxybipheny-4-yl)-3-phenyl-3-(4-pyrrolidinophenyl)naphtha[2,1-b]pyran (0.6 g, 1 mmol) in DCM (50 mL), 4-dimethylaminopyridine and pyridine (1 mL) at 0° C. with stirring. Stirring was continued for 1 h and the solution poured into HCl (1 M, 50 mL), extracted with DCM (2×50 ml), washed with water (50 ml), dried ($MgSO_4$) and the solvent removed under reduced pressure. The residue was chromatographed on silica using DCM (70% in hexanes) as eluent. The solvent was removed under reduced pressure and the residue crystallised from hexanes to give the title compound (0.39 g, 44%) as a colourless powder, mp 90-91° C.

Example (i)

[4'-(perfluorobutanesulfonyloxy)biphen-4-yl]-3-phenyl-3-(4-pyrrolidinophenyl)-3H-naphtho[2,1-b]pyran

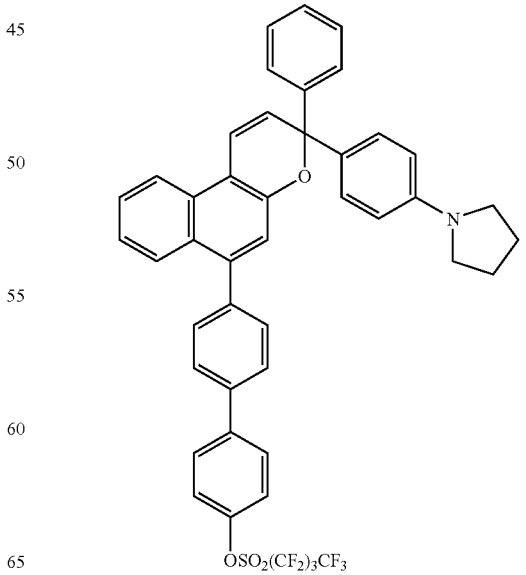

(i)

Perfluorobutansulfonyl fluoride (0.276 g, 0.8 mmol) was added to a solution of 6-(4-hydroxybipheny-4-yl)-3-phenyl-3-(4-pyrrolidinophenyl)naphtha[2,1-b]pyran (0.35 g, 0.6 mmol) in DCM (15 mL) and Et$_3$N (0.5 mL) at 0° C. with stirring. Stirring was continued for 2 days and the solution poured into HCl (2 M, 100 mL), extracted with DCM (3×50 ml), washed with water (100 ml), dried (MgSO$_4$) and the solvent removed under reduced pressure. The residue was filtered through a short plug of silica using DCM (40% in hexanes) as eluent. The solvent was reduced and decanted. The residue was pumped to dryness to give the title compound (0.16 g, 31%) as a violet powder, mp 92-93° C.

The invention claimed is:
1. A naphthopyran compound represented by the formula (I)

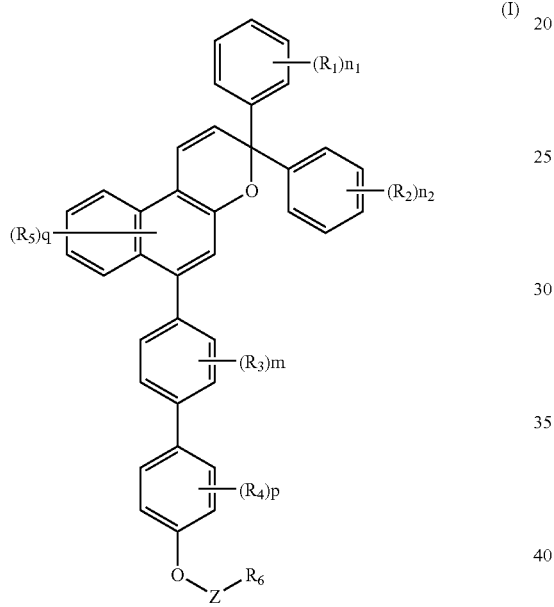

wherein:
$n_1$ is an integer comprised from 0 to 5 inclusive;
$n_2$ is an integer comprised from 0 to 5 inclusive;
p is an integer comprised from 0 to 4 inclusive;
m is an integer comprised from 0 to 4 inclusive;
q is an integer comprised from 0 to 5 inclusive;
$R_1$, $R_2$ and $R_4$, identical or different, independently from each other, represent a group selected from halogen, —$R_a$, —OH, —O$R_a$, —SH, —S$R_a$, —NH$_2$, —N$R_a R_{a1}$, —N$R_b R_c$, —CO—$R_a$, —CO$_2 R_{a1}$, —OC(O)—$R_d$, —X—($R_e$)—Y, linear or branched (C$_1$-C$_{18}$) perfluoroalkyl group, wherein:
$R_a$ represents a linear or branched (C$_{1-18}$) alkyl group;
$R_{a1}$ represents a group selected from hydrogen and linear or branched (C$_{1-18}$) alkyl group;
$R_b$ and $R_c$,
together and in combination with the nitrogen atom, represent a saturated 5 to 7 membered heterocyclic group which comprises optionally one additional heteroatom selected from O, N and S, and which may be optionally substituted by one or two group(s), identical or different, selected from halogen, —$R_a$, —OH, —O$R_a$, —NH$_2$, and —N$R_a R_{a1}$, wherein $R_a$ and $R_{a1}$ are as defined hereinbefore, or together and in combination with the nitrogen atom and the adjacent phenyl group form a heterocyclic group of formula (A), (B), (C) or (D) wherein t is an integer comprised from 0 to 2 inclusive:

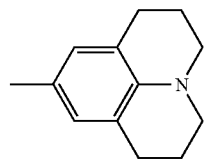

(A)

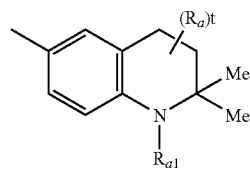

(B)

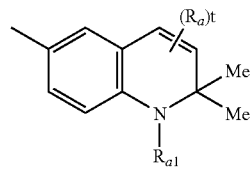

(C)

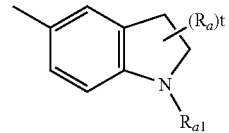

(D)

X represents a group selected from oxygen atom, —N($R_{a1}$)—, sulphur atom, —S(O)— and —S(O$_2$)— wherein $R_{a1}$ is as defined hereinbefore;
Y represents a group selected from –O$R_{a1}$, —N$R_{a1} R_{a2}$, and —S$R_{a1}$ wherein $R_{a1}$ is as defined hereinbefore and $R_{a2}$ represent a group selected from hydrogen and linear or branched (C$_{1-18}$) alkyl group;
$R_e$ represents a linear or branched (C$_1$-C$_{18}$) alkylene group, which may be optionally substituted by a group selected from halogen, hydroxyl, linear or branched (C$_1$-C$_6$) alkoxy, and amino;
$R_d$ represents a group selected from linear or branched (C$_{1-18}$) alkyl group, —($R_e$)—Y, and aryl group which is optionally substituted by 1 to 4 groups selected from halogen, —$R_a$, —OH, —O$R_a$, —SH, —S$R_a$, —NH$_2$, —N$R_a R_{a1}$, —N$R_b R_c$, —CO—$R_a$, —CO$_2 R_{a1}$ wherein $R_a$, $R_{a1}$, $R_b$, $R_c$, $R_d$, $R_e$ and Y are as defined hereinbefore;
$R_3$ represents a group selected from halogen, —$R_a$, linear or branched (C$_{1-18}$) perfluoroalkyl group —OH, —O$R_a$, —SH, —S$R_a$, —NH$_2$, and —N$R_a R_{a1}$, wherein $R_a$ and $R_{a1}$ are as defined hereinbefore;
$R_6$ represents a group selected from:
—$R_a$ which may be optionally substituted by a group selected from halogen, —OH, —O$R_a$, —SH, —S$R_a$, —NH$_2$, —N$R_a R_{a1}$, —CO—$R_a$, and —CO$_2 R_{a1}$, wherein $R_a$ and $R_{a1}$ are as defined hereinbefore;
linear or branched (C$_{1-18}$) perfluoroalkyl group;
cycloalkyl, heterocycloalkyl, aryl, heteroaryl, which may be optionally substituted by 1 to 4 groups selected from halogen, —OH, —O$R_a$, —SH, —S$R_a$, —NH$_2$, —N$R_a R_{a1}$, —CO—$R_a$, —O—C(O)—$R_a$ and —CO$_2 R_{a1}$, $R_5$ represents a group selected from:
- halogen, —$R_a$, linear or branched ($C_{1-18}$) perfluoroalkyl group, —OH, —$OR_a$, —SH, —$SR_a$, —$NH_2$, —$NR_aR_{a1}$, —CO—$R_a$, —O—C(O)—$R_a$ and —$CO_2R_{a1}$ wherein $R_a$ and $R_{a1}$ are as defined hereinbefore,
- or when q is equal to 2 and then two $R_5$ substituents are located onto two adjacent carbon atoms selected from C-7, C-8, C-9 and C-10 of the naphtho[2,1-b]pyran group, they may further represent together a group —O—$(CH_2)_{q1}$—O— wherein q1 represents an integer comprised from 1 to 3 inclusive;

Z represents a group selected from CO, CS, SO, $SO_2$, $CO_2$, C(O)S, $CS_2$, C(O)NH, C(O)$NR_a$, C(S)NH, C(S)$NR_a$ and C=$NR_a$, wherein $R_a$ is as defined hereinbefore.

2. The naphthopyran compound according to claim 1, wherein:
- $n_1$ is equal to 0 or 1, and $R_1$ represents a group selected from halogen, —OH and —$OR_a$ located at the para- or ortho-position of the phenyl group, wherein $R_a$ is as defined hereinbefore;
- $n_2$ is equal to 1 and $R_2$ represents a group selected from halogen, —OH, —$OR_a$, and —$NR_bR_c$ located at the para-position of the phenyl group, wherein $R_a$, $R_b$ and $R_c$ are as defined hereinbefore;
- m is equal to zero;
- p is equal to zero;
- q is an integer comprised from 0 to 2 inclusive, and $R_5$ represents a group selected from —OH and —$OR_a$ located on the C-8 and/or C-9 of the naphtho[2,1-b]-pyran group;
- $R_6$ represents a group selected from —$R_a$, a linear or branched ($C_{1-18}$) perfluoroalkyl group, aryl, heteroaryl, which may be substituted by 1 to 4 groups selected from halogen and —$OR_a$ wherein $R_a$ is as defined hereinbefore; and
- Z represents a group selected from CO and $SO_2$.

3. The naphthopyran compound of claim 1 which is selected from one of the following compounds:
- 6-[4'-(4-Butoxybenzoyloxy)-4-biphenyl]-3-[4-(hexyloxy)phenyl]-3-[4-(4-methylpiperidino)phenyl]-3H-naphtho[2,1-b]pyran;
- 6-[4'-(4-Dodecanoyloxy)-4-biphenyl]-3-[4-(hexyloxy)phenyl]-3-[4-(4-methylpiperidino)phenyl]-3H-naphtho[2,1-b]pyran;
- 6-[4'-(perfluorooctanoyloxy)biphen-4-yl]-3-phenyl-3-(4-pyrrolidinophenyl)-3H-naphtho[2,1-b]pyran;
- 6-[4'-(perfluorododecanoyloxy)biphen-4-yl]-3-phenyl-3-(4-pyrrolidinophenyl)-3H-naphtho[2,1-b]pyran;
- 3-(4-fluorophenyl)-6-(4'-(hexanoyloxy)biphen-4-yl)-3-phenyl-3H-naphtho[2,1-b]pyran;
- 8,9-dimethoxy-6-[4'-(4,4,5,5,6,6,7,7,7-nonafluoroheptanoyloxy)biphen-4-yl]-3-phenyl-3-(4-pyrrolidinophenyl)-3H-naphtho[1,2-b]pyran;
- 8,9-dimethoxy-6-[4'-(2,4-difluorobenzoyloxy)biphen-4-yl]-3-phenyl-3-(4-pyrrolidinophenyl)-3H-naphtho[1,2-b]pyran;
- 6-[4'-(stearoyloxy)biphen-4-yl]-3-phenyl-3-(4-pyrrolidinophenyl)-3H-naphtho[2,1-b]pyran; and
- [4'-(perfluorobutanesulfonyloxy)biphen-4-yl]-3-phenyl-3-(4-pyrrolidinophenyl)-3H-naphtho[2,1-b]pyran.

4. Ophthalmic lens comprising at least one naphthopyran compound according to claim 1.

5. Ophthalmic lens according to claim 4, comprising a polymeric host material, the at least one naphthopyran compound being incorporated in the bulk of said polymeric host material.

6. Ophthalmic lens according to claim 5, wherein the polymeric host material is selected from polymers of polyol(allyl carbonate) monomers, polyacrylates, poly(triethyleneglycol dimethacrylate), polyperfluoroacrylates, cellulose acetate, cellulose triacetate, cellulose acetate propionate, cellulose acetate butyrate, poly(vinyl acetate), poly(vinyl alcohol), polyurethanes, polycarbonates, poly(ethylene terephthalate), polystyrene), polyfluorostyrene, poly(diethylene glycol bis (alkyl carbonate)) and mixtures thereof.

7. Ophthalmic lens according to claim 4, comprising an optical substrate and at least one film or coating comprising the at least one naphthopyran compound.

8. Ophthalmic lens according to claim 7, wherein the at least one film or coating is a dichroic film or coating comprising an anisotropic oriented polymer layer and the at least one naphthopyran compound.

9. Ophthalmic lens according to claim 4, comprising a fluid, mesomorphous or gel host medium incorporating the at least one naphthopyran compound.

10. Ophthalmic lens according to claim 9, wherein the fluid or mesomorphous host medium incorporating the at least one naphthopyran compound is selected from the group consisting of organic solvents, liquid crystals, liquid crystal polymers and mixtures thereof.

11. Ophthalmic lens according to claim 10, which is a device containing a mechanism for holding the mixture of the host medium and dye in a mechanically stable environment.

12. Ophthalmic lens according to claim 11, comprising a pair of opposed substrates having a gap there between for receiving the mixture of the host medium and the at least one photochromic dye and a frame for holding said pair of substrates adjacent one another.

13. Ophthalmic lens according to claim 11, comprising an optical component provided with at least one transparent cell arrangement juxtaposed in a parallel direction to the surface thereof, each cell being tightly closed and containing said fluid host medium and said at least one naphthopyran compound.

14. Ophthalmic lens according to claim 13, wherein the transparent cell arrangement forms a layer whose height perpendicular to the component surface is less than 100 µm.

15. Ophthalmic lens according to claim 13, wherein said optical component comprises a transparent rigid substrate whereon is formed the transparent cell arrangement.

16. Ophthalmic lens according to claim 13, wherein said optical component comprises a transparent rigid substrate and, applied on said substrate, a transparent film incorporating the transparent cell arrangement.

17. Ophthalmic lens according to claim 13 wherein the ratio of the total surface occupied by the cells to the total surface of the optical component is at least 90%.

18. Ophthalmic lens according to claim 13 wherein the cells have a size of at least 1 µm parallel to the surface of the optical component.

19. Ophthalmic lens according to claim 13 wherein the cells are separated from each other by means of partitions having a thickness of 0.10 to 5.00 µm.

20. Ophthalmic lens according to claim 13 which is selected from the group consisting of ophthalmic elements and devices, display elements and devices, windows or mirrors.

21. Ophthalmic lens according to claim 14, wherein the transparent cell arrangement forms a layer whose height perpendicular to the component surface is comprised between 1 µm and 50 µm.

22. Ophthalmic lens according to claim 17, wherein the ratio of the total surface occupied by the cells to the total surface of the optical component is comprised between 90 and 99.5%.

23. Ophthalmic lens according to claim 22, wherein the ratio of the total surface occupied by the cells to the total surface of the optical component is comprised between 96% and 98.5%.

24. Ophthalmic lens according to claim 18, wherein the cells have a size comprised between 5 μm and 100 μm, parallel to the surface of the optical component.

25. Ophthalmic lens according to claim 20, which is selected from the group consisting of lenses.

26. Ophthalmic lens according to claim 25, which is selected from the group consisting of ophthalmic lenses.

27. Ophthalmic lens according to claim 9, wherein the fluid or mesomorphous host medium incorporating the at least one naphthopyran compound comprises a nematic liquid crystal media.

* * * * *